United States Patent
Paul et al.

(10) Patent No.: US 11,016,157 B2
(45) Date of Patent: May 25, 2021

(54) MAGNETIC RESONANCE METHOD AND APPARATUS FOR SUPPRESSING METAL ARTIFACTS

(71) Applicant: Siemens Healthcare GmbH, Erlangen (DE)

(72) Inventors: Dominik Paul, Bubenreuth (DE); Flavio Carinci, Erlangen (DE); Mario Zeller, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 18 days.

(21) Appl. No.: 16/515,444

(22) Filed: Jul. 18, 2019

(65) Prior Publication Data

US 2020/0025849 A1   Jan. 23, 2020

(30) Foreign Application Priority Data

Jul. 19, 2018   (EP) .................................. 18184365

(51) Int. Cl.
| | | |
|---|---|---|
| *G01R 33/483* | (2006.01) | |
| *A61B 5/055* | (2006.01) | |
| *G01R 33/36* | (2006.01) | |
| *G01R 33/561* | (2006.01) | |
| *G01R 33/565* | (2006.01) | |

(Continued)

(52) U.S. Cl.
CPC .......... *G01R 33/4835* (2013.01); *A61B 5/055* (2013.01); *G01R 33/36* (2013.01); *G01R 33/5611* (2013.01); *G01R 33/56536* (2013.01); *G06T 11/008* (2013.01); *G01R 33/385* (2013.01)

(58) Field of Classification Search
CPC ........................ G01R 33/4835; G01R 33/36; G01R 33/5611; G01R 33/56536; A61B 5/055; G06T 11/008
See application file for complete search history.

(56) References Cited

U.S. PATENT DOCUMENTS 6,487,435 B2 * 11/2002 Mistretta ............ G01R 33/4824
  324/307
6,671,536 B2 * 12/2003 Mistretta ................ G01R 33/28
  128/898

(Continued)

OTHER PUBLICATIONS

Hargreaves, Brian A. et al., "Accelerated Slice Encoding for Metal Artifact Correction"; Journal of Magnetic Resonance Imaging; 2010; vol. 31; pp. 987-996.

(Continued)

*Primary Examiner* — Dixomara Vargas
(74) *Attorney, Agent, or Firm* — Schiff Hardin LLP (57) ABSTRACT

A method and system for suppressing metal artifacts in magnetic resonance (MR) images of slices of a patient containing a metallic implant. The method and system can use a Slice Encoding for Metal Artifact Correction (SEMAC) sequence. In the method and system, MR data of each slice is fully sampled in k-space in a reference region located in a center of k-space in a phase-encoding direction and a central section in a slice-selection direction. The MR-data of each slice outside the reference region can be undersampled in k-space. The fully sampled MR data from the reference regions of each slice can be combined to generate a reference data set for reconstructing an MR image of each slice.

16 Claims, 6 Drawing Sheets

(51) Int. Cl.
*G06T 11/00* (2006.01)
*G01R 33/385* (2006.01)

(56) References Cited

U.S. PATENT DOCUMENTS

| | | | | |
|---|---|---|---|---|
| 6,983,182 B2* | 1/2006 | Mistretta | ............ | G01R 33/5635 600/425 |
| 7,343,193 B2* | 3/2008 | Block | ................ | G01R 33/5601 324/306 |
| 7,622,924 B2* | 11/2009 | Hwang | .............. | G01R 33/5611 324/307 |
| 7,649,354 B2* | 1/2010 | Bayram | ................ | G01R 33/561 324/309 |
| 7,688,068 B2* | 3/2010 | Beatty | .................... | A61B 5/055 324/307 |
| 8,089,278 B1* | 1/2012 | Du | ...................... | G01R 33/4824 324/307 |
| 8,502,534 B2* | 8/2013 | Lai | ...................... | G01R 33/5611 324/309 |
| 9,429,636 B2* | 8/2016 | Ivancevic | ........ | G01R 33/56316 |
| 9,478,051 B2* | 10/2016 | Li | ......................... | G01R 33/561 |
| 9,964,621 B2* | 5/2018 | Basha | ................ | G01R 33/4824 |
| 10,215,822 B2* | 2/2019 | Takeshima | ......... | G01R 33/4818 |
| 10,302,713 B2* | 5/2019 | Popescu | ........... | G01R 33/5611 |
| 10,368,778 B2* | 8/2019 | Li | ......................... | G01R 33/022 |
| 10,670,678 B2* | 6/2020 | Beck | ................. | G01R 33/5601 |
| 10,746,831 B2* | 8/2020 | Pipe | .......................... | G01V 3/14 |
| 2001/0027262 A1* | 10/2001 | Mistretta | ............ | G01R 33/4824 600/9 |
| 2003/0013953 A1* | 1/2003 | Mistretta | ................. | A61B 6/469 600/425 |
| 2003/0060698 A1* | 3/2003 | Mistretta | ................ | G01R 33/28 600/410 |
| 2004/0254447 A1* | 12/2004 | Block | ................. | G01R 33/563 600/410 |
| 2009/0001984 A1* | 1/2009 | Hwang | ............ | G01R 33/56545 324/307 |
| 2009/0082656 A1* | 3/2009 | Bayram | ............... | G01R 33/561 600/410 |
| 2011/0241670 A1* | 10/2011 | Lai | ...................... | G01R 33/5611 324/309 |
| 2012/0262167 A1 | 10/2012 | Lai et al. | | |
| 2015/0097565 A1* | 4/2015 | Basha | ................ | G01R 33/4824 324/322 |
| 2015/0204961 A1* | 7/2015 | Ivancevic | ............ | G01R 33/385 324/309 |
| 2015/0279065 A1* | 10/2015 | Li | ...................... | G01R 33/5611 382/131 |
| 2016/0245882 A1* | 8/2016 | Popescu | ............ | G01R 33/5611 |
| 2017/0336488 A1* | 11/2017 | Pipe | ................... | G01R 33/4824 |
| 2018/0092569 A1* | 4/2018 | Li | ......................... | G01R 33/022 |
| 2018/0149721 A1* | 5/2018 | Beck | ................. | G01R 33/4826 |

OTHER PUBLICATIONS

Breuer, Felix A. et al., "Controlled Aliasing in Volumetric Parallel Imaging (2D CAIPIRINHA)", Magnetic Resonance in Medicine, vol. 55, pp. 549-556, 2006 // DOI: 10.1002/mrm.20787.

Ricardo Otazo et al: "Sparse-SEMAC: rapid and improved SEMAC metal implant imaging using SPARSE-SENSE acceleration: Sparse-SEMAC", Magnetic Resonance in Medicine., vol. 78, No. 1, Jul. 25, 2016 (Jul. 25, 2016), pp. 79-87, XP055554614, US; ISSN: 0740-3194, DOI: 10.1002/mrm.26342.

Breuer, Felix A. et al., "Controlled Aliasing in Parallel Imaging Results in Higher Acceleration (CAIPIRINHA) for Multi-Slice Imaging" Magnetic Resonance in Medicine, vol. 53, No. 3, pp. 684-691, 2005 // DOI: 10.1002/mrm.20401.

Lu, Wenmiao et al., "SEMAC: Slice Encoding for Metal Artifact Correction in MRI", Magnetic Resonance in Medicine, vol. 62, pp. 66-76, 2009.

European search report dated Feb. 28, 2019, Application No. EP 18184365.7.

* cited by examiner

MAGNETIC RESONANCE METHOD AND APPARATUS FOR SUPPRESSING METAL ARTIFACTS

CROSS REFERENCE TO RELATED APPLICATIONS

This patent application claims priority to European Patent Application No. 18184365.7, filed Jul. 19, 2018, which is incorporated herein by reference in its entirety.

BACKGROUND

Field

The present disclosure relates to a magnetic resonance (MR) method and apparatus for suppressing metal artifacts, including a MR imaging method and apparatus that make use of a Slice Encoding for Metal Artifact Correction (SEMAC) technique for suppressing metal artifacts in a MR image of a patient containing a metallic implant.

Related Art

Magnetic resonance imaging (MRI) provides very good soft-tissue contrast, and accordingly can be used for examination of metallic implants in a patient. However, metal-induced artifacts, such as distortion, signal voids, and pile-up artifacts, often render MR images unusable for diagnostic purposes. These metal artifacts exist both in in-plane and through-slice direction, resulting from static field inhomogeneities near metal implants due to the susceptibility difference between tissues and metal.

A variety of common MR techniques for suppression of metal-induced artifacts in MRI are used in clinical practice. The use of spin echoes recovers much of the signal loss and is used in orthopedic imaging. View-angle tilting (VAT), as disclosed in the document "Phase error corrected interlaced echo planar imaging" by Cho, Z. H., et al. in Proc., SMRM, 6th Annual Meeting, New York. 1987, is an effective method to suppress in-plane distortion, but does not correct through-plane distortion. Numerous methods that estimate a distortion map have been proposed, but these in general assign a distortion field to each pixel, which is inadequate for rapid spatial variations of the static magnetic field. In many cases, maximizing the slice-selection and readout bandwidths can reduce artifacts, but at a cost of the signal-to-noise ratio (SNR). However, the range of frequencies around metallic implants typically exceed the excitation pulse bandwidth, such that is impossible to correct distortion and avoid signal loss without increasing the amount of data acquired.

In order to suppress through-plane metal artifacts in Spin Echo (SE)-based sequences, such as the Turbo Spin Echo (TSE) method, a Slice Encoding for Metal Artifact Correction (SEMAC) technique can be used, as described, for examine, in the documents "Accelerated slice encoding for metal artifact correction" Hargreaves, Brian A., et al. in Journal of Magnetic Resonance Imaging 31.4 (2010): 987-996 and "SEMAC: Slice Encoding for Metal Artifact Correction in MRI" by Lu, W., et al. in Magnetic Resonance In Medicine 62, pp. 66-76, 2009. Such SEMAC techniques involve carrying out an additional coding in slice selection direction (z-direction) while using a conventional two-dimensional protocol or slice-based scan. The additional coding corresponds to a phase coding and is also known as "SEMAC-encoding." With this technique, the scanning time increases linearly with the number of additional phase encoding steps, i.e. with the number of additional SEMAC readout volumes, corresponding to each slice, in slice-selection direction, which are also referred to as SEMAC steps. A suitable number of SEMAC steps, however, is necessary in order to completely resolve image artifacts caused by the metallic implant in the patient, and therefore it is not possible to simply reduce the number of SEMAC coding steps in order to reduce the measurement time. Particularly in the case of T2-weighted TSE protocols with a long repetition time (TR), the total measurement time increases significantly.

For example, in a T2-weighted TSE protocol that already includes 256 phase coding steps with a turbo factor of 8 and a repetition time of 4,000 ms, an acquisition time of 2 minutes, 8 seconds is required. It is to be noted that in this respect 8 SEMAC steps usually are not sufficient, where according to clinical experience, 13 to 19 SEMAC steps, for example, are used for high-quality metal artefact suppression. If a SEMAC resolution of, for example, 16 steps is selected for use in such a protocol, the measurement time increases to over 34 minutes, which is significantly longer than is acceptable in most clinical or hospital environments.

Therefore, the need exists for an improved method for suppressing metal artifacts, which has a reduced scanning time and better efficiency in suppressing metal artifacts in MR images of a patient containing a metallic implant.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure.

According to an exemplary embodiment of the disclosure, a method for operating an MR apparatus is provided. In this example, MR images of a plurality of slices of an examination person are generated using a Slice Encoding for Metal Artifact Correction (SEMAC) sequence, where each slice is associated with a corresponding plurality of sections in a slice-selection direction. Therein, for each slice, MR data is acquired from the corresponding plurality of sections, where the MR data is fully sampled in k-space in a reference region, which is located in a center of k-space in phase-encoding direction and a central section in slice-selection direction, and where the MR-data outside the reference region is undersampled in k-space. In an exemplary embodiment, the method includes combining the fully sampled MR data from the reference regions of each slice to generate a reference data set. Then a MR image of each slice is reconstructed using the MR data of the corresponding slice and the reference data set.

By the above method according to an exemplary embodiment of the disclosure, MR image acquisition is significantly accelerated by a reduction of reference lines needed for MR image reconstruction, in particular by using symmetries and analogies in the MR data of each slice acquired in a SEMAC sequence. By the use of redundant data for the creation of the reference data set according to the disclosure, an improved method for suppressing metal artifacts in a MR image of a patient containing a metallic implant is provided, which has reduced scanning time and better efficiency in suppressing metal artifacts.

The reference region in the center of k-space in phase-encoding direction can be a part, or only a part, of the acquired k-space in phase-encoding direction. In other words, the reference region can refer to a central part, or subset, of the acquired k-space in phase-encoding direction, or of a line of the acquired k-space in phase-encoding direction, wherein the reference region is smaller than the complete acquired k-space in phase-encoding direction. It can be located centrally in the central section with regard to the k-space center. In particular, the reference region in phase-encoding direction can be only 1/16 to 4/16 of the acquired k-space in phase-encoding direction, further in particular 1/8 of the acquired k-space in phase-encoding direction.

By reducing the reference region, in which k-space is fully sampled, measurement steps, i.e. phase-encoding steps, are spared and thus the measurement time can be advantageously reduced. 1/16 to 1/4 of the acquired k-space in phase-encoding direction, in particular 1/8, are especially advantageously balanced between MR image quality, i.e. metal artefact suppression, and MR measurement time.

The central section in slice-selection direction can be a part, or only a part, of the acquired k-space in slice-selection direction and can be located in the center of k-space in slice-selection direction. The central section can comprise the slice of the examining person, or it can comprise a section besides the corresponding slice of the examining person, and is situated in the middle of, or between, the other sections corresponding to the respective slice.

By reducing the reference region, in which k-space is fully sampled, measurement time is advantageously reduced, and by choosing only the central section corresponding to each slice, and choosing the location of the central section as the middle or center section of the corresponding sections, symmetry and analogy between the slices can be advantageously used, where the quantity of fully sampled k-space data can be reduced and at the same time maintain quality of metal artefact suppression and reduce MR measurement time.

In an exemplary embodiment, the slices of the examination person (i.e. person under examination) can be adjacent to each other, which enables a faster and more efficient data processing of the reconstructed MR images.

In an exemplary embodiment, at least one of the sections corresponding to a first slice can be overlapping in slice-selection direction with at least one of the sections corresponding to a second slice adjacent to the first slice. In this example, the sections of at least two slices can be overlapping each other, whereby efficient and high quality metal artefact removal is enabled.

The MR image of a slice is reconstructed from the MR data from the corresponding sections using the reference data set based on a GRAPPA (GeneRalized Autocalibrating Partial Parallel Acquisition), or a CS (compressed sensing)/SENSE (SENSitivity Encoding) technique. Accordingly, the reference data set, or only the reference data set, can be used together with the undersampled MR data for calculating the GRAPPA weights, GRAPPA kernels, or coil sensitivities for MR image reconstruction in each slice. A combination of SEMAC with GRAPPA or CS/SENSE based on the reduced reference data according to the disclosure thus enables fast and more efficient MR imaging.

In an exemplary embodiment, the reference data set is transformed using Fourier-Transformations in phase direction and read-out direction into an MR image with lower resolution than the images for each slice for calculating coil sensitivities, thus enabling efficient MR image reconstruction.

In an exemplary embodiment, the process of combining the fully sampled MR data from the reference regions of each slice to generate a reference data set includes attaching the fully sampled MR data of each reference region directly adjacent to each other in a matrix, where the MR data of each slice is located in the matrix according to the order of the corresponding slices in slice-selection direction. The fully sampled MR data of each section can be an adjacent line or column in the matrix. In an exemplary embodiment, the reference data set includes only the fully sampled MR data from the reference regions of each slice. By the reference data set as described above, MR image reconstruction can be based on reduced MR data, in particular on a reduced number of reference lines, where generation of the reference data set is more efficient and easier than in conventional SEMAC techniques.

In an exemplary embodiment, MR data in the SEMAC sequence is acquired according to a Spin Echo (SE)-based data acquisition technique, and thereby provides an efficient MR imaging method near metal implants of a patient.

In an exemplary embodiment of the disclosure, a magnetic resonance (MR) apparatus is provided. In an exemplary embodiment, MR apparatus is configured to generate MR images of a plurality of slices of an examination person using a Slice Encoding for Metal Artifact Correction (SEMAC) sequence. In this example, each slice is associated with a corresponding plurality of sections in a slice-selection direction. In an exemplary embodiment, the MR apparatus includes a controller. In an exemplary embodiment, the controller includes a computer with a memory and at least one processor, where the memory contains instructions (or can be provided with instructions) and the processor(s) is configured to execute the instructions to perform the following operations to generate MR image(s). In an exemplary embodiment, apparatus is configured to acquire, for each slice, MR data from the corresponding sections, where the MR data is fully sampled in k-space in a reference region that is located in a center of k-space in phase-encoding direction and a central section in slice-selection direction, and where the MR-data outside the reference region is undersampled in k-space. In an exemplary embodiment, the apparatus is further configured to combine the fully sampled MR data from the reference regions of each slice to generate a reference data set. In an exemplary embodiment, the apparatus is further configured to reconstruct an MR image of each slice using the MR data of the corresponding slice and the reference data set. In an exemplary embodiment, the controller includes processor circuitry that is configured to perform one or more operations/functions of the controller and/or control one or more components of the MR apparatus to perform one or more operations of the MR apparatus as described herein.

By using the reference data set according to the disclosure, the MR apparatus is operative to suppress metal artefacts in MR images near metallic implants in a more efficient way compared to a conventional MR apparatus, so as to provide a reduced scanning time while efficiently suppressing the metal artifacts in MR images. MR image acquisition by the MR apparatus is significantly accelerated by a reduction of reference lines needed for image reconstruction of each slice, in particular by using symmetries and analogies in the MR data of each slice acquired during a SEMAC technique.

In an exemplary embodiment, the magnetic resonance (MR) apparatus is configured to perform any one or any combination of the methods/operations described in one or more aspects/embodiments of the present disclosure as would be understood by one of ordinary skill in the relevant arts.

In an exemplary embodiment of the disclosure, a computer program product including program code to be executed by at least one processor of a computer of an MR apparatus is provided, where execution of the program code causes the at least one processor to execute a method according to any one or any combination of the methods/operations described one or more aspects/embodiments of the present disclosure as would be understood by one of ordinary skill in the relevant arts.

In an exemplary embodiment of the disclosure, a non-transitory computer-readable data storage medium encoded with programming instructions is provided, where the data storage medium can be loaded into a control computer of a magnetic resonance (MR) apparatus, and the execution of the programming instructions by the control computer causes the MR apparatus to execute a method according to any one or any combination of the aspects/embodiments of the present disclosure as would be understood by one of ordinary skill in the relevant arts.

With such a computer program product and non-transitory computer-readable data storage medium for suppressing metal artifacts in operation of an MR imaging apparatus, technical effects can be achieved, which correspond to the technical effects described in the various embodiments herein.

It is the aim of SEMAC techniques to correct signal loss and distortion artifacts, which result from metal-induced magnetic field inhomogeneities. Near metal, there is a range of resonant frequencies that results in frequency shifts $\Delta f$ of the magnetic spins, and consequently in image distortion, signal loss, and signal pile-up artifacts in both the slice-selection direction and the readout direction. In the phase-encoding direction, however, there are no distortions, since phase differences induced by phase-encode gradients are independent of field inhomogeneities.

To correct through-plane distortion, a SEMAC technique can be used, wherein resonant frequency shifts $\Delta f$ have a maximum of $+/-\Delta f max$. A finite-width slice 1 of thickness $\Delta s$ is excited, using an RF pulse of bandwidth BWRF. When distortions are considered, the slice may now excite a range $\pm \Delta fmax \Delta s/BWRF$. To resolve this profile, we add additional phase encoding in the slice direction spanning a FOV (field of view) z, which we will refer to as SEMAC phase encoding. After acquisition and a Fourier transform in the SEMAC phase-encoding (slice or z) direction, we have resolved the actual z signal locations, which we will refer to as sections 2. The spatially resolved sections 2 from all excited slices are then added to form an image with no through-plane distortion.

A slice-selection direction 6 within the meaning of the present disclosure may refer to the z-direction, the through-plane direction, wherein also the SEMAC phase-encoding direction is in slice-selection direction.

A section 2 within the meaning of the present disclosure may refer to a SEMAC measurement volume, or SEMAC section, which corresponds to a part, or part of a line, of the acquired k-space in SEMAC phase-encoding direction.

Figure 1:
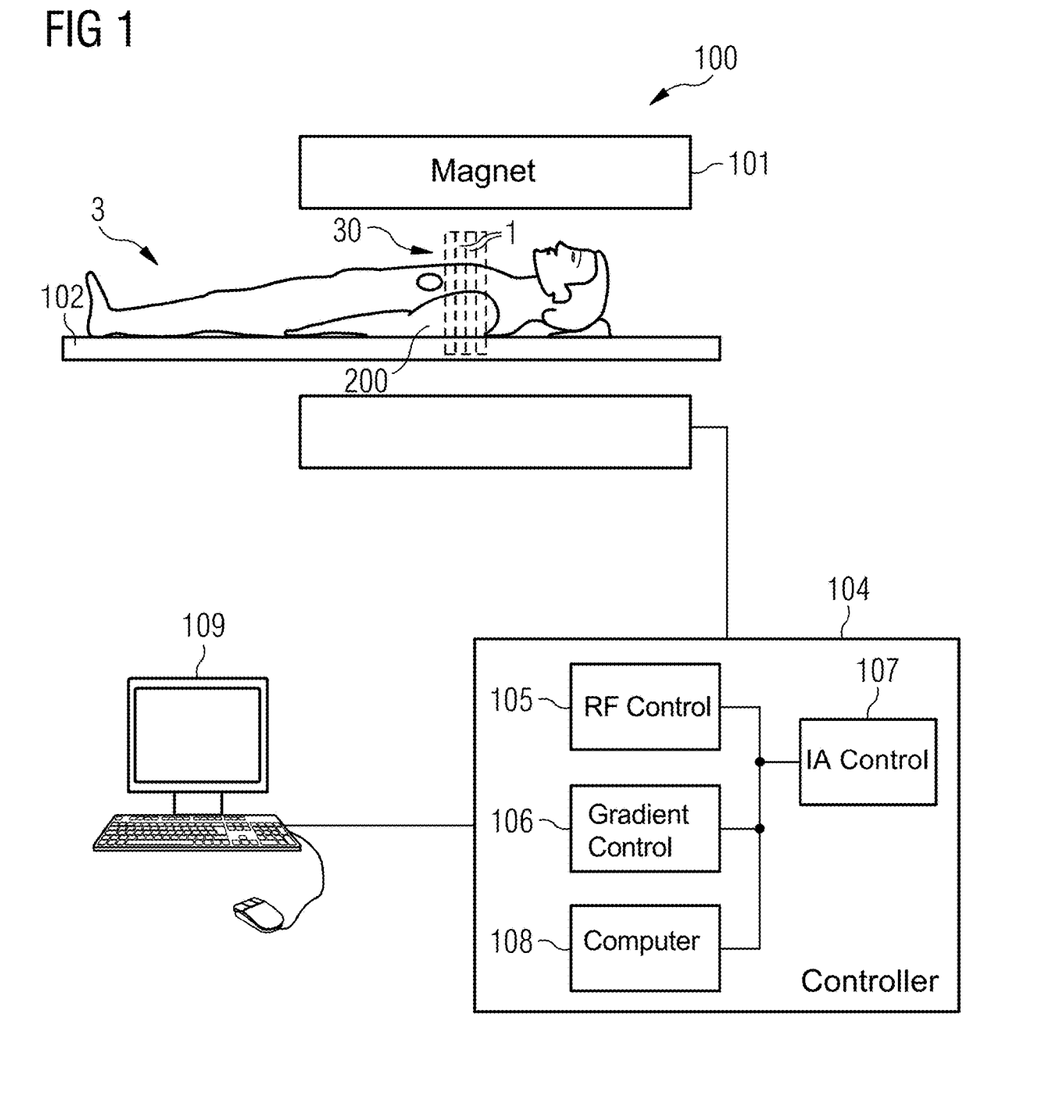
FIG. 1 schematically illustrates an MR apparatus according to exemplary embodiments of the present disclosure.

FIG. 1 schematically illustrates an MR apparatus 100 according to exemplary embodiments of the present disclosure.

An MR apparatus 100 with which metal artifacts in a MR image of a patient 3 containing a metallic implant can be efficiently suppressed in an MRI examination according to the disclosure is shown in FIG. 1.

In an exemplary embodiment, the MR imaging system 100 has a basic field magnet 101 that generates a polarization field B0. An examination person 3 arranged on a patient table 102 is driven into the center of the basic field magnet 101 where the acquisition of the MR signals from an examination region is implemented via radiation of RF pulses and switching of magnetic gradients. A plurality of slices 1 (i.e. slabs) to be examined by the MR apparatus 100 are arranged in a staple 30 of slices 1, where for each of the slices 1, an MR image is generated. The generation of MR images—in particular, images of tissue containing a metallic implant—can use a pulse sequence with a series of RF pulses and switching of magnetic gradients according to a SEMAC technique as would be understood by one of ordinary skill in the art and therefore discussion of such generations are omitted for brevity.

In an exemplary embodiment, The MR imaging system 100 is connected with a central controller 104 with which the MR system 100 is controlled. Among other entities, the central controller 104 comprises an RF controller 105, which controls the switching of RF pulses to excite the magnetization. A gradient controller 106 controls the switching of the gradient magnetic fields for spatial coding of the excited spins. An imaging acquisition controller 107 controls the workflow of the gradient switching, the RF pulses, and the MR signal readout depending on a selected MR imaging sequence. In an exemplary embodiment, the controllers 104, 105, 106, and/or 107 include processor circuitry that is configured to perform one or more functions/operations of the respective controller.

In an exemplary embodiment, computer 108 processes MR signals, or MR data, from the examining region and calculates MR images from the MR data in a known manner via Fourier transformation from the MR data detected with a coil (not shown), wherein the images can be displayed on a display 109. In an exemplary embodiment, the computer 108 includes processor circuitry that is configured to perform one or more functions/operations of the computer 108. In an exemplary embodiment, the MR imaging system 100 is controlled by an operator. The other typical components of an MR system have been omitted for clarity. The method operations described in the following in connection with FIG. 1 can, for example, be implemented with the aid of the computer 108 in one or more embodiments.

Figure 2:
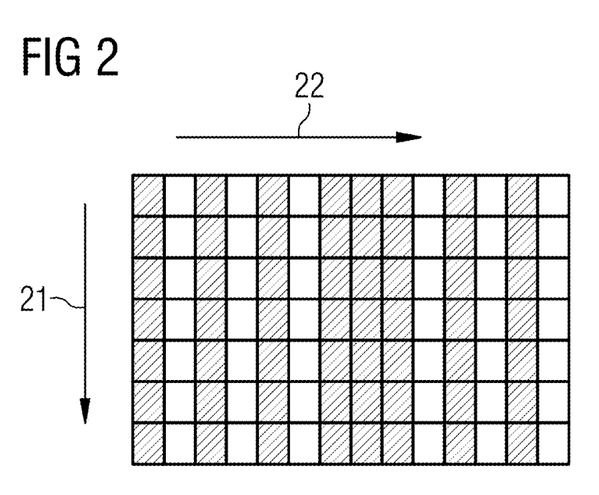
FIG. 2 illustrates a sampling scheme of a SEMAC technique in combination with a conventional Parallel Imaging Technique (PAT) according to exemplary embodiments of the present disclosure.

FIG. 2 illustrates a sampling scheme of a SEMAC technique in combination with a conventional Parallel Imaging Technique (PAT), according to exemplary embodiments of the disclosure.

Image acquisition time is one of the most important considerations for clinical MRI examinations. The development of multi coil hardware as well as dedicated parallel acquisition techniques (PAT) and respective reconstruction methods allowed for significant decrease of acquisition times in almost all clinical practice.

Parallel imaging techniques (PAT) are robust methods for accelerating the acquisition of MR imaging data, where in PAT, the amount of k-space data is reduced, often by a factor of two or greater, by acquiring a reduced number of sampled k-space lines with an array of receiver coils, where the number of phase-encoding steps are reduced. This undersampled data can be acquired more quickly, but the undersampling leads to aliased images. One of several parallel imaging algorithms can then be used to reconstruct artifact-free images from either the aliased images (SENSE-type reconstruction) or from the undersampled data (GRAPPA-type reconstruction). The advantages of parallel imaging in a clinical setting include faster image acquisition, which can be used, for instance, to shorten breath-hold times resulting in fewer motion-corrupted examinations.

According to the conventional PAT sampling scheme shown in FIG. 2, the phase-encoding direction 22 is from left to right, and the SEMAC direction 21, which is the slice—select direction or z-direction, is top-down. It can be seen in FIG. 2 that in the center of the phase-encoding direction k-space is fully sampled, wherein in the outer regions the MR data is undersampled in phase-encoding direction.

Figure 3:
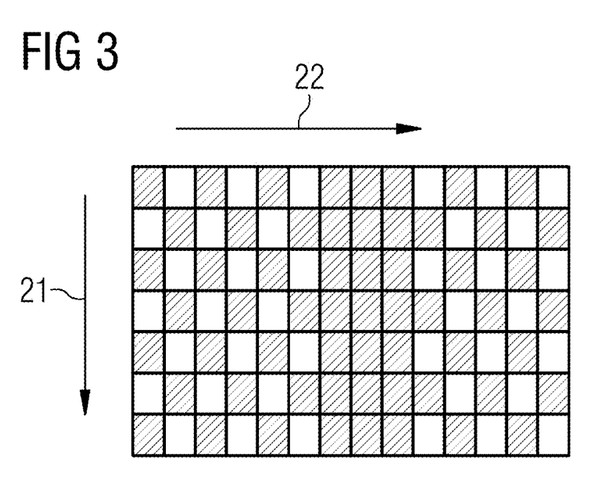
FIG. 3 illustrates a sampling scheme of a SEMAC technique in combination with a CAIPIRINHA technique according to exemplary embodiments of the present disclosure.

FIG. 3 illustrates a sampling scheme of a SEMAC technique in combination with a Controlled Aliasing In Parallel Imaging Results IN Higher Acceleration (CAIPIRINHA) technique, according to embodiments of the disclosure.

In an exemplary embodiment, SENSE and GRAPPA can be performed in 3D acquisition mode using acceleration in two phase-encoding directions simultaneously. The Controlled Aliasing In Parallel Imaging Results IN Higher Acceleration (CAIPIRINHA) techniques allow to partially overcome the limitations of conventional PAT techniques by modifying the aliasing conditions in a defined way. This leads to an improved g-factor when compared to standard acquisition with the same acceleration factor. CAIPIRINHA takes effect already during the data acquisition by modifying the RF excitation or gradient encoding scheme in order to use the coil encoding power of the underlying receiver array to full capacity. The concept has been successfully applied so far to 3D MR imaging, where data reduction can be carried out in two phase-encoding directions (2D-CAIPIRINHA), as described in the document "Controlled aliasing in volumetric parallel imaging (2D CAIPIRINHA)" by Breuer et al in Magn Reson Med. 2006, March; 55(3):549-56, and simultaneous multi-slice imaging (MS-CAIPIRINHA), as described in the document "Controlled Aliasing in Parallel Imaging Results in Higher Acceleration (CAIPIRINHA) for Multislice Imaging" by Breuer F A, et al in Magn Reson Med 2005; 53:684-691.

According to the CAIPIRINHA sampling scheme shown in FIG. 3, the phase-encoding direction 22 is from left to right, and the SEMAC direction 21, which is the slice—selection direction or z-direction, is top-down. It can be further seen in FIG. 3 that in the center of the phase-encoding direction there is a fully sampled part in k-space, wherein in the outer regions the MR data is undersampled in phase-encoding direction 22 and SEMAC direction 21.

Figure 4:
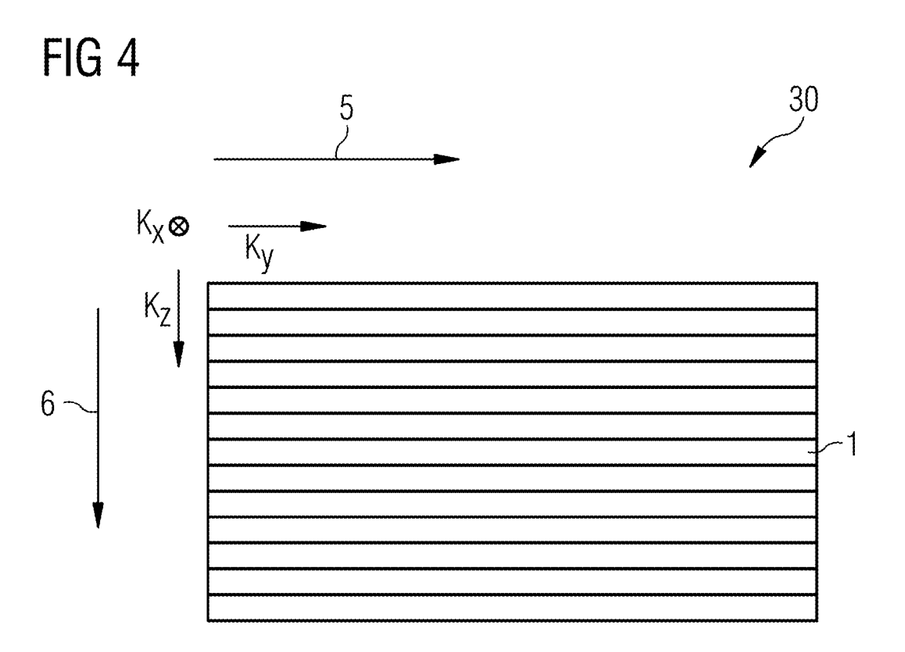
FIG. 4 illustrates the sampling scheme according to a SEMAC technique according to exemplary embodiments of the present disclosure.

FIG. 4 illustrates the sampling of k-space of a SEMAC technique, according to exemplary embodiments of the disclosure.

As illustrated in FIG. 4, the objective of a SEMAC technique is to acquire, where possible, all the spins that are excited by a selective excitation of slice 1. Because of magnetic field inhomogeneities, the spins excited by the selective excitation are located in a volume section that is at least partially distorted and displaced with respect to originally targeted layer-like slice 1. For this reason, according to the SEMAC method, further read-out volumes, which can correspond to other slices 1, in other words SEMAC sections 2 corresponding to slice 1, in the Kz direction in the vicinity of the respective slice are also sampled and spatially resolved in k-space by use of a SEMAC magnetic field gradient in z-direction.

Each slice 1 shown in FIG. 4 corresponds to a designated phase-encoding step in the slice selection direction Kz 6, i.e. to a designated SEMAC gradient moment with respect to the SEMAC phase-encoding gradient, which is active in the Kz direction. In order to acquire the MR data related to a slice 1, a designated number of phase-encoding steps are necessary along a second direction Ky 5. For each of these phase-encoding steps, a k-space line in a third direction Kx is selected, the first direction Kz or slice selection direction, the second direction Ky and the third direction Kz being reciprocally perpendicular to one another.

Figure 5:
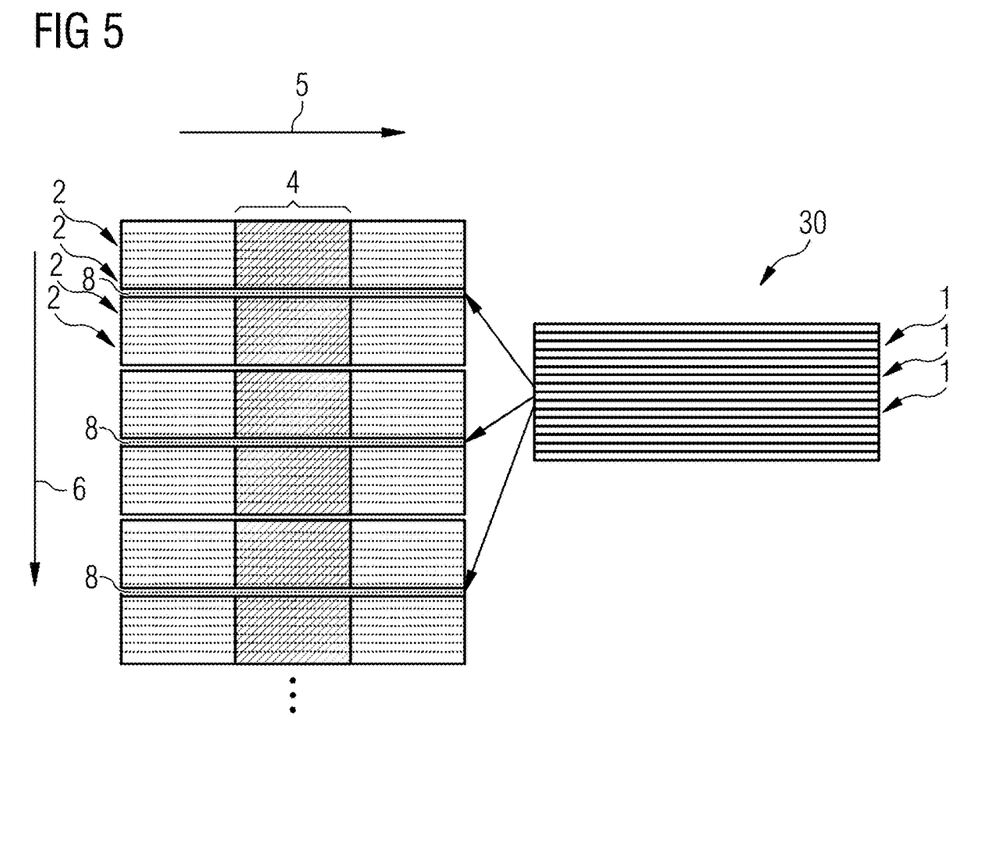
FIG. 5 illustrates a sampling scheme of a conventional SEMAC technique.

FIG. 5 illustrates a sampling scheme of a conventional SEMAC technique.

In FIG. 5, a staple 30 of slices 1 is depicted, which corresponds to the staple 30 of slices 1 of an examination person 3, or in general an examination object, as shown in FIG. 1. The slices 1 can, in one or more embodiments, be directly adjacent to each other. The slices 1 are to be examined by a MR apparatus in order to generate a two-dimensional MR image of each of the slices 1. On the left side in FIG. 5, for a respective slice 1 in slice-selection direction 6, k-space of a single SEMAC measurement of slice 1 including a plurality of corresponding SEMAC sections 2 is depicted, wherein Ky or phase-encoding direction 5 is from left to right, SEMAC phase-encoding direction 6 is from top to bottom. In this embodiment, a central section 8 corresponds to a respective slice 1, where it is to be noted that the SEMAC sections 2 around central section 8 of a first slice 1 are overlapping the SEMAC sections 2 of a second slice 1 adjacent to the first slice 1. In other embodiments, central section 8 can be any section, which is located in the center of sections 2. In some embodiments, the central section 8 can refer to a single central section 2 in z-direction, which is located in a central position in k-space in SEMAC phase-encoding direction 6.

The SEMAC phase-encoding space, which is defined by phase-encoding direction 5 and SEMAC phase encoding direction 6, is used to acquire fully sampled reference data for MR image reconstruction. Conventionally, the area for reference data is approximately 11 to 19 steps in SEMAC direction 6, wherein the upper number of steps is usually limited by time available for the measurement, and 24 to 48 steps in phase-encoding direction 5.

As depicted in FIG. 5, in a center 4 of k-space in phase-encoding direction 5, which is a central part of the acquired k-space in phase-encoding direction 5, conventionally, k-space is sampled fully in each section 2, in order to generate a conventional reference data set for MR image reconstruction for the slice 1. Further, reference data for each slice 1 is sampled separately for each slice 1 in such a way, in order to generate a separate conventional reference data sets for each slice 1, wherein no symmetry or analogy of the data between the plurality of slices 1 is used.

Figure 6:
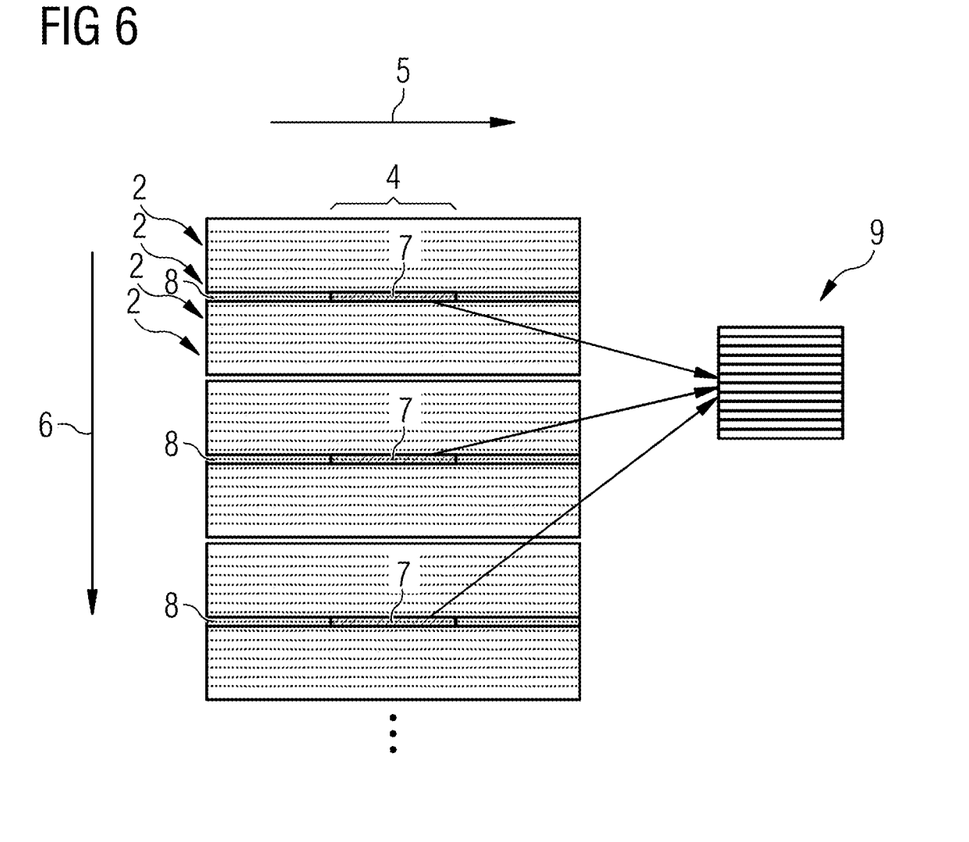
FIG. 6 illustrates a sampling scheme of a SEMAC technique according to exemplary embodiments of the present disclosure.

FIG. 6 illustrates a sampling scheme of a SEMAC technique according to exemplary embodiments of the disclosure.

According the disclosure, the measurement time of the reference data is advantageously reduced, where less MR data is recorded for each slice 1, and where redundant information between the slices 1 is used at the same time. In an exemplary embodiment, fully sampled reference data is only recorded for the central SEMAC step 8 for each slice 1. The reference data from each slice 1 is then combined into a larger artificial reference data set 9. The reference data set 9 can then be used to determine the GRAPPA kernels or, for CS/SENSE, the coil sensitivities for MR image reconstruction of each slice 1. Since the slices 1 in SEMAC are directly adjacent, the MR reference data of each slice 1 can be sorted directly into a matrix. In an exemplary embodiment, the new reference data set is then transformed into the image space, i.e. into a low-resolution image, by a Fourier transformation in two or three directions (phase-encoding directions and read-out direction) to calculate the coil sensitivities. Similarly, the data can be used to calculate the GRAPPA weights.

As shown in FIG. 6, k-space for each slice 1 is fully sampled in k-space only in a reference region 7, which is located in a center 4 of k-space in phase-encoding direction 5 and a central section 8 in slice-selection direction 6, and wherein the MR-data outside the reference region 7 is undersampled in k-space in a phase-encoding direction. In other words, in sections 2 other than the central section 8, and in regions in the central section 8 outside the reference region 7, the acquired MR-data is undersampled in a phase-encoding direction. Thus, the number of reference lines is reduced compared to conventional SEMAC techniques.

In one or more exemplary embodiments, the central section 8 in slice-selection direction 6 is only a small part the acquired k-space in slice-selection direction 6. Accordingly, the central section 8 can be located at the center of k-space acquired for the corresponding plurality of sections 2 in slice-selection direction 6. The central section 8 can be a central line in k-space, it can include the corresponding slice 1 of the examining person, or it can be a section 2 besides the corresponding slice 1 of the examining person, it can be situated in the middle of, or between, the other sections 2 corresponding to the respective slice 1.

In an exemplary embodiment, the fully sampled MR data from each of the reference regions 7 of each slice 1 is combined into a matrix to generate artificial reference data set 9, which can then be used for reconstructing an MR image of each slice 1 from the undersampled MR data of the corresponding slice 1.

According to an exemplary embodiment, MR measurement data corresponding to a k-space Matrix with 256 steps in phase-encoding direction and 13 steps in SEMAC encoding direction is acquired, where a conventional reference area is 32×13 with PAT 2. Therefore, in a conventional SEMAC measurement 256*13/2+32*13/2=1872 phase encoding steps have to be performed. According to an exemplary embodiment the disclosure only 256*13/2+32/2=1680 phase encoding steps have to be performed, which results in a reduction in phase encoding steps of 11%.

Figure 7:
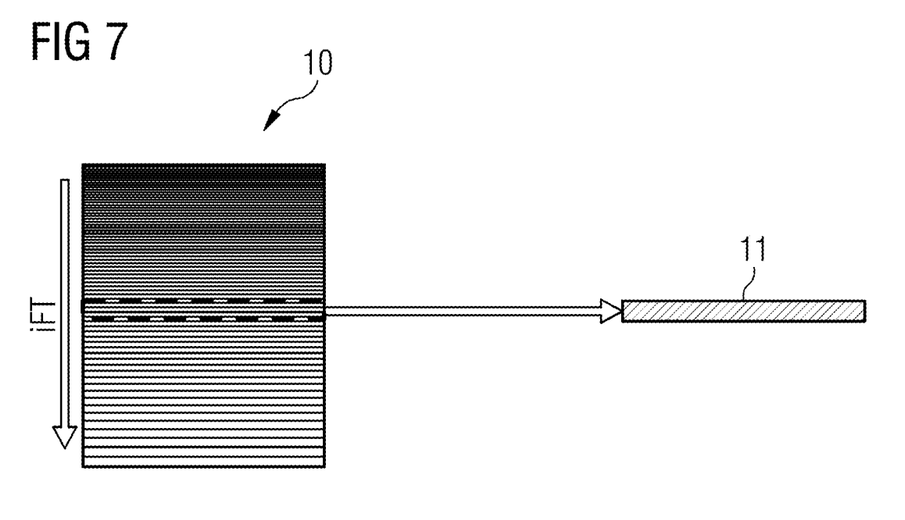
FIG. 7 illustrates a reference data set after inverse Fourier transformation in SEMAC direction, according to exemplary embodiments of the present disclosure.

FIG. 7 illustrates a reference data set 9 after inverse Fourier transformation in SEMAC direction. In FIG. 7, the central line in the transformed reference region, shown in dotted lines, corresponds to reference line 11 at the same geometric position.

Figure 8:
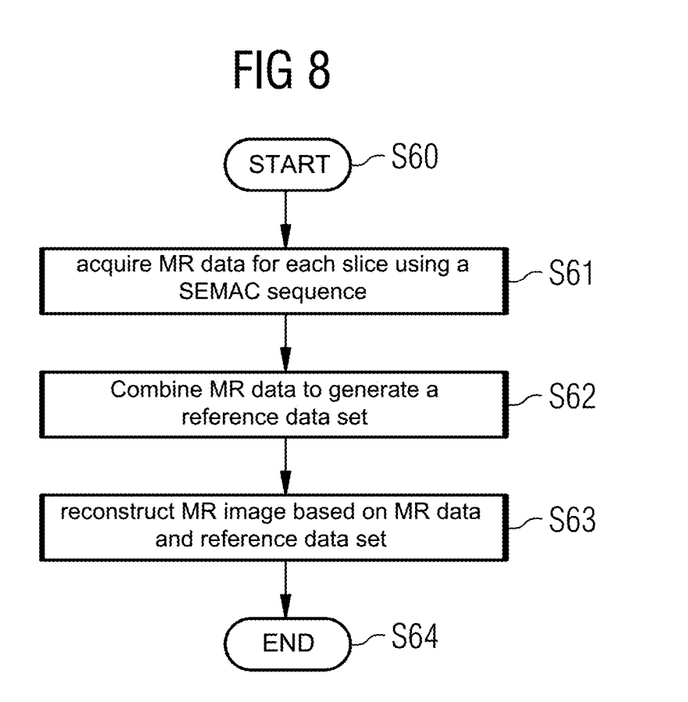
FIG. 8 illustrates a flow chart of a method for suppressing metal artefacts in an MRI examination according to exemplary embodiments of the present disclosure.

FIG. 8 illustrates a flow chart of the method for suppressing metal artefacts in an MRI examination, according to exemplary embodiments of the disclosure.

In an exemplary embodiment, the method starts with step S60. In step S61, for each slice, MR data is acquired, using a Slice Encoding for Metal Artifact Correction (SEMAC) sequence, from a plurality of SEMAC sections corresponding to the respective slice 1. In this example, for each slice 1, the MR data is fully sampled in k-space in a reference region 7, which is located in a center of k-space in phase-encoding direction 5 and a central section 8 in slice-selection direction 6. In an exemplary embodiment, the MR-data outside the reference region 7 is undersampled in k-space. In step S62, the fully sampled MR data from the reference regions 7 of each slice 1 is combined to generate a reference data set 9. In step S63, an MR image of each slice 1 is reconstructed using the MR data of the corresponding slice 1 and the reference data set 9. The method ends with step S64.

In the field of MRI, according to the present disclosure, a new method for suppressing metal artifacts in MR images of slices of a patient containing a metallic implant using a Slice Encoding for Metal Artifact Correction (SEMAC) sequence is provided. Therein, MR data of each slice is fully sampled in k-space only in a reference region, which is located in a center of k-space in phase-encoding direction and a central section in slice-selection direction, and where the MR-data of each slice outside the reference region is undersampled in k-space. The fully sampled MR data from the reference regions of each slice is combined to generate a reference data set for reconstructing an MR image of each slice. Thereby, MR image acquisition is significantly accelerated by a reduction of reference lines needed for image reconstruction of each slice, in particular by using symmetries and analogies in the MR data of each slice. The method according to the disclosure has a reduced scanning time and better efficiency in suppressing the metal artifacts.

CONCLUSION

The aforementioned description of the specific embodiments will so fully reveal the general nature of the disclosure that others can, by applying knowledge within the skill of the art, readily modify and/or adapt for various applications such specific embodiments, without undue experimentation, and without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computers, processors, controllers, or other devices executing the firmware, software, routines, instructions, etc. Further, any of the implementation variations may be carried out by a general purpose computer.

For the purposes of this discussion, the term "processor circuitry" shall be understood to be circuit(s), processor(s), logic, or a combination thereof. A circuit includes an analog circuit, a digital circuit, state machine logic, programable processing circuit, other structural electronic hardware, or a combination thereof. A processor includes a microprocessor, a digital signal processor (DSP), central processing unit (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A method for operating a magnetic resonance (MR) apparatus configured to generate MR images of a plurality of slices of an examination person using a Slice Encoding for Metal Artifact Correction (SEMAC) sequence, each slice being associated with a corresponding plurality of sections in a slice-selection direction, the method comprising:
in a computer of the MR apparatus, for each slice, acquiring MR data from the corresponding plurality of sections, the MR data being fully sampled in k-space in a reference region located in a center of k-space in a phase-encoding direction and a central section in a slice-selection direction, wherein the MR data outside the reference region is undersampled in k-space;
in the computer, combining the fully sampled MR data from the reference regions of each slice to generate a reference data set; and
in the computer, reconstructing an MR image of each slice using the MR data of the corresponding slice and the reference data set.

2. The method according to claim 1, wherein the reference region in the center of k-space in the phase-encoding direction is a part of the acquired k-space in the phase-encoding direction.

3. The method according to claim 1, wherein the central section in the slice-selection direction is a part of the acquired k-space in the slice-selection direction and is located in the center of k-space in the slice-selection direction.

4. The method according to claim 1, wherein the slices of the examination person are adjacent to one another.

5. The method according to claim 1, wherein at least one of the sections corresponding to a first slice overlaps, in the slice-selection direction, with at least one of the sections corresponding to a second slice adjacent to the first slice.

6. The method according to claim 1, wherein the MR image of one of the slices is reconstructed from the MR data from the corresponding sections based on the reference data set using a GeneRalized Autocalibrating Partial Parallel Acquisition (GRAPPA) technique.

7. The method according to claim 4, wherein only the reference data set is used to calculate GeneRalized Autocalibrating Partial Parallel Acquisition (GRAPPA) weights for the MR image reconstruction in each slice.

8. The method according to claim 1, wherein the MR image of a slice is reconstructed from the MR data of the corresponding sections using the reference data set based on a compressed sensing (CS)/SENSitivity Encoding (SENSE) technique.

9. The method according to claim 8, wherein the reference data set is transformed using Fourier-Transformations, in the phase-encoding direction and a read-out direction, into an MR image with lower resolution than the MR images for each slice for calculating coil sensitivities.

10. The method according to claim 1, wherein combining the fully sampled MR data from the reference regions of each slice to generate the reference data set comprises:
attaching the fully sampled MR data of each reference region of the reference regions directly adjacent to each other in a matrix, wherein the MR data of each slice is located in the matrix according to an order of the corresponding slices in the slice-selection direction.

11. The method according to claim 10, wherein each fully sampled MR data of each section is an adjacent line or column in the matrix.

12. The method according to claim 1, wherein the reference data set comprises only the fully sampled MR data from the reference regions of each slice.

13. The method according to claim 1, wherein the MR data in the SEMAC sequence is acquired according to a Spin Echo (SE)-based data acquisition technique.

14. The method according to claim 1, further comprising generating, by the computer, an electronic output signal corresponding to one or more of the reconstructed MR images.

15. A non-transitory computer-readable data storage medium encoded with programming instructions that when executed by at least one processor causes the at least one processor to perform the following operations using a of a magnetic resonance (MR) apparatus configured to generate MR images of a plurality of slices of an examination person using a Slice Encoding for Metal Artifact Correction (SEMAC) sequence, each slice being associated with a corresponding plurality of sections in a slice-selection direction, the operations comprising:

for each slice, acquiring MR data from the corresponding plurality of sections, the MR data being fully sampled in k-space in a reference region located in a center of k-space in a phase-encoding direction and a central section in a slice-selection direction, wherein the MR data outside the reference region is undersampled in k-space;

combining the fully sampled MR data from the reference regions of each slice to generate a reference data set; and reconstructing an MR image of each slice using the MR data of the corresponding slice and the reference data set.

16. A magnetic resonance (MR) apparatus for generating magnetic resonance (MR) images of a plurality of slices of an examination person using a Slice Encoding for Metal Artifact Correction (SEMAC) sequence, each slice being associated with a corresponding plurality of sections in a slice-selection direction, the MR apparatus comprising:

a memory that stores instructions; and
a processor communicatively coupled to the memory and configured to execute the instructions to:

for each slice, acquire MR data from the corresponding plurality of sections, the MR data being fully sampled in k-space in a reference region located in a center of k-space in a phase-encoding direction and a central section in a slice-selection direction, wherein the MR-data outside the reference region is undersampled in k-space;

combine the fully sampled MR data from the reference regions of each slice to generate a reference data set; and reconstruct an MR image of each slice using the MR data of the corresponding slice and the reference data set.

* * * * *